United States Patent [19]

Scheucher et al.

[11] Patent Number: 5,239,876
[45] Date of Patent: Aug. 31, 1993

[54] APPARATUS FOR DETERMINING THE PROPERTIES OF A COMPACTIBLE MATERIAL

[75] Inventors: Peter Scheucher, Albersdorf; Franz Petschauer, Lannach; Alois Pesdicek, Frohnleiten, all of Austria

[73] Assignees: Andritz-Patentverwaltungs-Gesellschaft, Graz, Austria; BTG Lausanne, S.A., Lausanne, Switzerland

[21] Appl. No.: 712,883

[22] Filed: Jun. 12, 1991

[30] Foreign Application Priority Data

Jun. 13, 1990 [AT] Austria .................. 1277

[51] Int. Cl.$^5$ .................................. G01N 1/10
[52] U.S. Cl. .................... 73/863.83; 73/864.43
[58] Field of Search ........... 73/863.83, 863.84, 864.43; 198/339.1, 346.1

[56] References Cited

U.S. PATENT DOCUMENTS

| | | | |
|---|---|---|---|
| 2,682,772 | 7/1954 | Peterson | 73/863.83 X |
| 2,720,109 | 10/1955 | Stirn et al. | 73/863.83 X |
| 3,062,045 | 11/1962 | Sökjer-Petersen et al. | 73/864.43 X |
| 3,129,590 | 4/1964 | Ellis | 73/863.83 |
| 3,447,381 | 6/1969 | Langtry et al. | 73/864.43 |
| 3,604,928 | 9/1971 | Starnes | 250/359.1 |
| 3,841,465 | 10/1974 | Miller, Jr. et al. | 198/213 |

FOREIGN PATENT DOCUMENTS

| | | | |
|---|---|---|---|
| 2742868 | 4/1979 | Fed. Rep. of Germany. | |
| 3329135 | 3/1984 | Fed. Rep. of Germany. | |
| 257857 | 11/1969 | U.S.S.R. | 73/864.43 |
| 379847 | 4/1973 | U.S.S.R. | 73/864.43 |
| 1019959 | 2/1966 | United Kingdom | 73/863.83 |

*Primary Examiner*—Tom Noland
*Attorney, Agent, or Firm*—Roylance, Abrams, Berdo & Goodman

[57] ABSTRACT

An apparatus for determining the properties of a compactible material in which the material is continuously conveyed through a measuring zone at substantially constant pressure is provided. The apparatus includes an auger type conveyor housed in a housing. The housing has an inlet, the measuring zone and an outlet. The conveyor removes the material from a container or pipe and conveys the material through the measuring zone. The apparatus includes a flow constrictor adjacent the measuring zone for increasing the pressure of and compacting the material in the measuring zone.

12 Claims, 4 Drawing Sheets

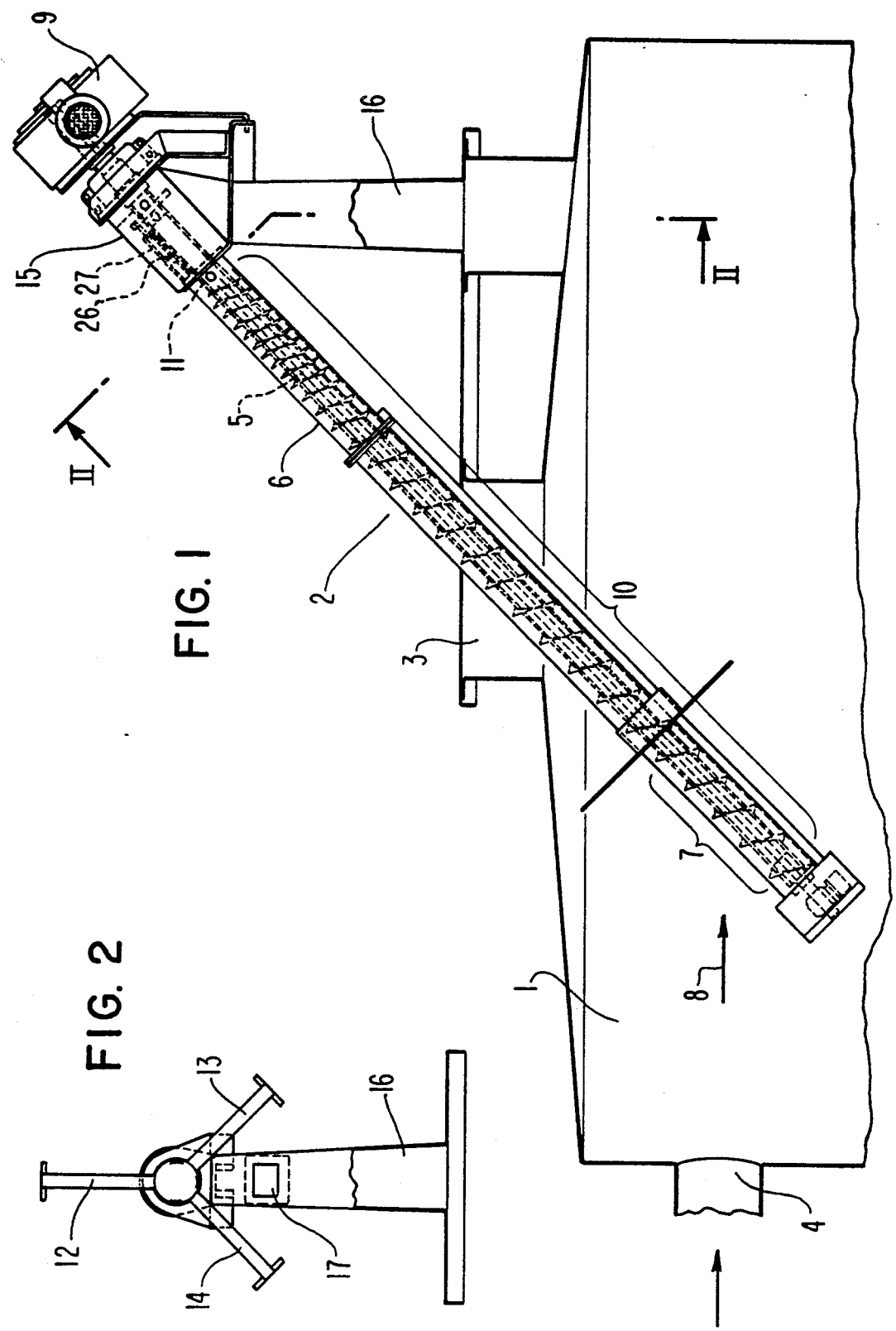

APPARATUS FOR DETERMINING THE PROPERTIES OF A COMPACTIBLE MATERIAL

FIELD OF THE INVENTION

This invention relates to apparatus for determining properties of a compactible material. More specifically, this invention relates to such an apparatus wherein a sample of the material is continuously passed through a measuring zone of the apparatus at a substantially constant rate by an auger type conveyor.

BACKGROUND OF THE INVENTION

It is often desirable to measure properties of a compactible material during the handling, transporting and/or treating of such material. Such measurements are sometimes accomplished by continuously removing a sample of the material from a container or pipe, continuously measuring the properties of the sample and returning the sample to the container or pipe.

Apparatus has been developed for this purpose which includes an auger type conveyor which extends into the material, removes a sampling of the material and conveys the sampling to a measurement station or measuring zone. Often the sampling is subjected to pressure and thus compacted at the measurement station to enhance the measurement process.

Known apparatus of this type, see for example DE-OS 33 29 135, have the drawback of an irregular pressure build-up in the measuring zone. In particular, the material is compacted up jamming the conveyor. In tests attempting to shorten the measuring zone, strong pressure fluctuations occurred and the actually intended pressure value temporarily dropped to zero such that no reliable measuring results could be obtained.

In order to obtain reliable measuring values, stable conditions are required with respect to the material conveyed through the measuring zone. Therefore, substantially isotropic conditions must be established in the measuring zone, particularly in the sensing range of the parameters to be determined.

SUMMARY OF THE INVENTION

The apparatus according to the present invention includes a housing having an inlet, an outlet and a measuring zone located between the inlet and outlet, a conveyor coupled to the housing for conveying material from the inlet of the housing, through the measuring zone and to the outlet of the housing, sensors attached to the measuring zone for determining specific properties of the material and a flow constrictor adjacent the measuring zone to increase the pressure of and compact the material.

In some embodiments of this invention, the flow constrictor is a disk biased against the material flow by at least one spring. The disk may be an annular ring concentric with the conveyor and may also be rotatably coupled to the conveyor.

In certain embodiments, the conveyor is an auger type conveyor. The spring may be a coil spring concentrically mounted on the shaft of the auger type conveyor. In the alternative, the spring may be comprised of a plurality of coil springs annularly located around the shaft of the conveyor. In yet other embodiments, the pressure-inducing element may be pneumatic or hydraulic bellows. The bellows can be hollow bodies suitable for charging with a fluid or an elastic ring.

In some embodiments, the disk and springs or bellows may be rotated independently of the conveyor. This may be particularly desirable if the disk or bellows is provided with projections such as ribs, for conveying the material.

If the conveyor extends through the disk or bellows, it may be formed in such a manner that it subjects the material to a comparatively low conveying energy and it may be formed as an S-screw conveyor with a low pitch.

In all of these embodiments, a gap is provided between the conveyor and the disk or bellows so that a certain amount of material presses therethrough. The pressure build-up in the measuring zone can be controlled not only by the disk or bellows, but also by the amount of material conveyed by the conveyor.

In or downstream of the measuring zone, baffles, such as webs, may be provided for obtaining a linear material transport in the measuring zone. This is particularly advantageous if the conveyor is a screw conveyor.

The apparatus according to this invention is mainly intended for carrying out measurements on materials removed from a main stream of material, conveyed through the measuring zone via a bypass and then returned to the main stream. The apparatus has particular application to the measuring of the properties of mixtures of fibrous materials such as chemical pulp and mechanical pulp, water, and/or treatment chemicals.

A preferred application of the apparatus according to the present invention is the measurement of the brightness and/or the residual content of chemicals (bleaching agents) of a pulp in parallel to the bleaching tower. This application applies to the production of chemical pulp and mechanical pulp.

The parameters determined in the measuring zone are processed in a conventional manner for process control. The parameters may be employed to adjust dwell times, temperatures, manner, and/or amount of chemicals added.

The invention is explained in detail in the following by means of several exemplary embodiments with reference to the accompanying drawing.

BRIEF DESCRIPTION OF THE DRAWINGS

FIG. 1 is an elevational view of one embodiment of a sampling device according to this invention affixed to the top part of a bleaching tower, with certain parts removed for clarity;

FIG. 2 is a cross-sectional view taken along line II—II in FIG. 1, illustrating sensing elements coupled to the measuring zone.

DESCRIPTION OF THE PREFERRED EMBODIMENTS

Figure 3:
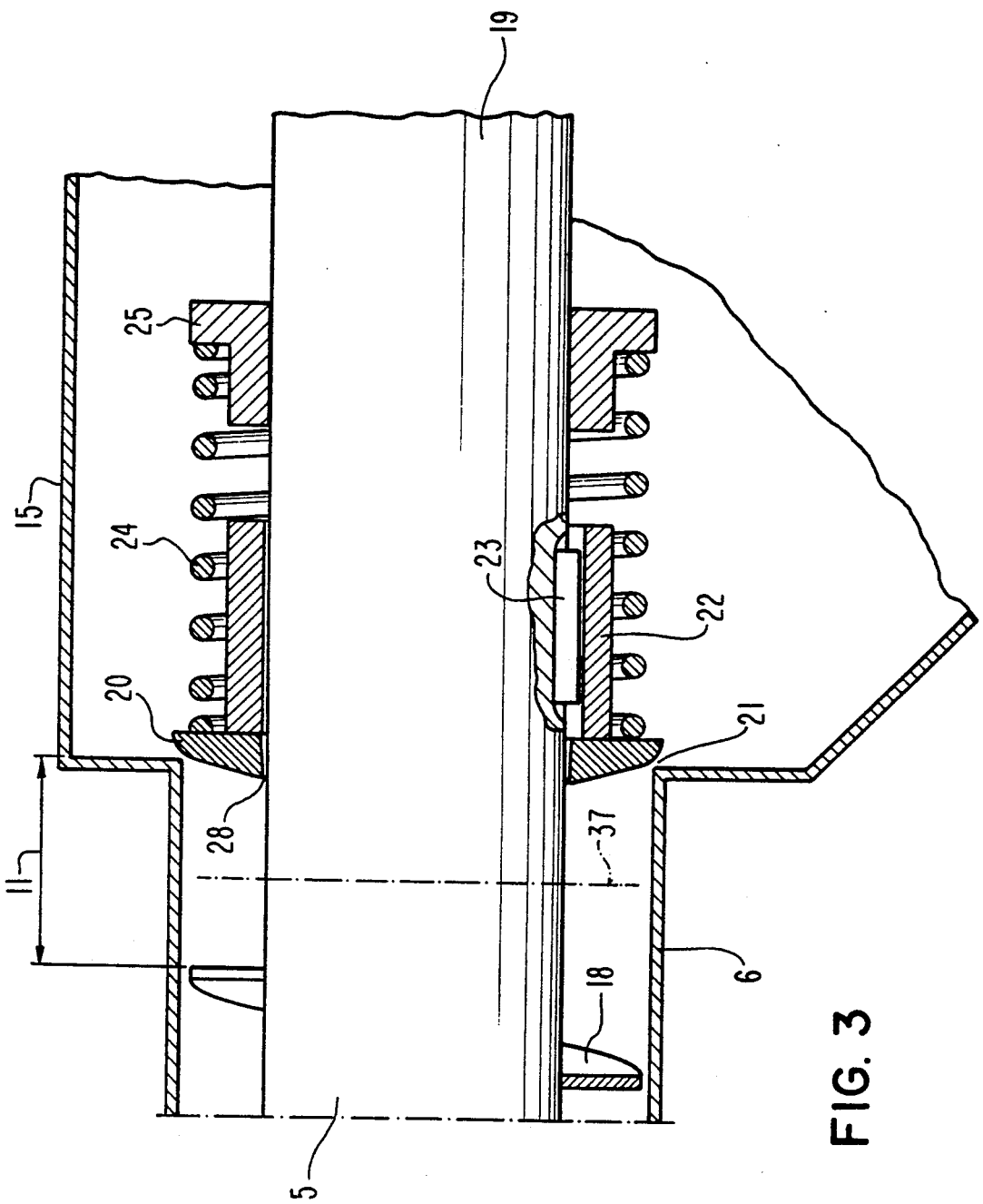
FIGS. 3, 4 and 5 are enlarged, cross-sectional views of three different embodiments of material flow constrictors disposed adjacent the measuring zone of the sampling device for creating a back pressure on the compactible material.

Referring to the Figures, and in particular FIG. 1, a sampling device 2 according to this invention is illustrated on a bleaching tower 1 containing compactible material. The sampling device 2 projects into the interior of the tower 1 and the compactible material within tower 1 through a central orifice 3 in the tower head.

The compactible material is charged into the tower 1 in such a manner that a sample of the compactible material can be received and conveyed by the conveyor 5 of the sampling device 2.

The sampling device 2 includes conveyor 5, tubular housing 6, variable speed motor 9, enlarged sleeve portion 15 and gravity pit 16.

In this embodiment, conveyor 5 is a screw or auger type conveyor rotatably supported in the tubular housing 6 and enlarged sleeve portion 15. Conveyor 5 extends from the lowermost end of tubular housing 6 through enlarged sleeve portion 15 and includes screw turns on a shaft 19.

The housing 6 is a hollow cylindrical housing having an opening or cut out 7 in the lower portion thereof. Material is charged into the bleaching tower 1 in the direction shown by arrow 8, received by conveyor 5 through opening 7, conveyed upwardly by conveyor 5 and then compacted during the rotation of the conveyor 5 in the housing 6 and enlarged sleeve portion 15, as discussed below.

The housing 6 includes a first zone, a conveying and compacting zone 10, followed by a second zone, the back-up or measuring zone 11. The conveyor 5 does not have screw turns in measuring zone 11, but continues as a smooth shaft up to the motor 9 as seen in the embodiments of FIGS. 1 and 3.

The desired parameters of the material are measured in measuring zone 11. In the case of a bleaching tower, the brightness of the pulp and the residual content of bleaching chemicals are measured. As seen in FIG. 2, three measuring studs 12, 13, and 14 extend radially from housing 6 at measuring zone 11. The measuring studs 12, 13 and 14 pierce through the wall of the measuring zone 11 from the outside and include conventional sensing elements (e.g., pressure transducer boxes). Such measuring studs and sensing elements are well known in this art, and thus are not described or illustrated in detail.

The variable speed motor 9 is provided at the upper end of enlarged sleeve portion 15 (described below) and is connected to shaft 19 of conveyor 5 for driving the conveyor 5.

In the embodiment illustrated in FIG. 3, enlarged sleeve portion 15 includes a partial continuation of tube 6 at a larger diameter, disk 20, sleeve 22, wedge 23, coil spring 24 and clamping ring 25.

Wedge 23 is affixed to shaft 19 of conveyor 5 and extends outwardly therefrom. Sleeve 22 is hollow and cylindrical and encompasses a portion of shaft 19. Sleeve 22 includes a recessed portion which receives and engages wedge 23. The recessed portion is designed such that sleeve 22 can move longitudinally relative wedge 23, and thus shaft 19, but rotates with shaft 19.

Disk 20 also encompasses a portion of shaft 19 and forms a ring around shaft 19. Disk 20 is welded to the sleeve 22 and thus rotates with shaft 19, but moves longitudinally relative shaft 19 with sleeve 22. As seen in FIG. 3, the edge 28 of the disk 20 adjacent shaft has very little clearance in relation to the shaft 19.

Disk 20 functions as a cross-section or flow constrictor. Disk 20 forms the end of the measuring zone 11 in the conveying direction of the material and closes this zone with the exception of an annular gap 21.

Clamping ring 25 also encompasses shaft 19 and is fixedly attached to shaft 19. Coil spring 24 encompasses shaft 19 and is attached at its ends to disk 20 and clamping ring 25.

Due to the small annular opening 21 between shaft 19 and disk 20, the material conveyed to the measuring zone 11 is compacted and placed under increased pressure in measuring zone 11. This pressure is a function in part of the spring force of coil spring 24. If the force or pressure of the material or disk 20 exceeds the spring force of spring 24, disk 20 is pushed away from the measuring zone 11 by the material, against the force of the spring 24, so that the annular opening 21 is widened. The pressure on the material is relieved after the material passes through the annular gap 21.

As a result of the movement of disk 20 as a function of the back-pressure of spring 24, constant pressure and throughput conditions in measuring zone 11 are established. The pressure in the measuring zone 11 and the volume of material pressing through gap 21 is in part a function of the number of revolutions per minute of the motor. It is possible to operate conveyor 5 at lower number of revolutions per minute at low capacities of material, utilizing a smaller annular gap 21, and at higher number of revolutions per minute at high capacities of material and utilizing a larger annular gap 21. Under all conditions, lower or higher volumes of material, the same respective pressure in measuring zone 11 can be achieved.

FIG. 1 illustrates another embodiment of enlarged sleeve portion 15 wherein, basically, a plurality of coil springs 26 spaced annularly around shaft 19 are substituted for the single coil spring of the embodiment illustrated in FIG. 2. Each coil spring 25 is received on a bolt 26 which passes through clamping ring 25. The spring force of springs 25 can be adjusted by bolts 26.

Figure 4:
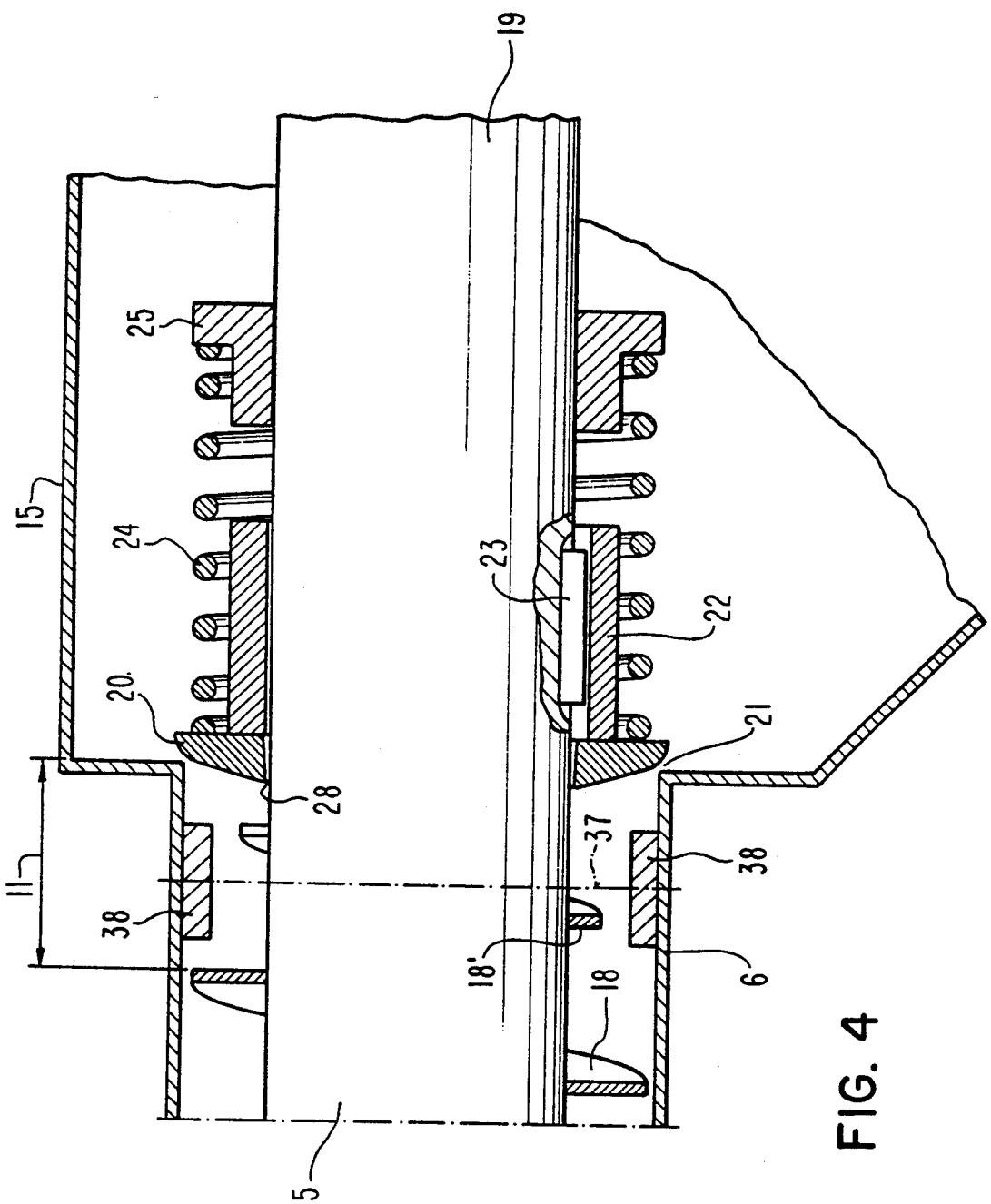

As seen in FIG. 4, another embodiment is illustrated. In this embodiment, the screw turns 18' of the conveyor 5 in the back-up or measuring zone 11 have a lower pitch and a lower height than the screw turns 18 in the conveying or compacting zone 10 to subject the material to a comparatively lower conveying energy. Furthermore, this embodiment includes a plurality of guiding members 38 for controlling the material flow in the back-up or measuring zone 11 such that the material moves axially through the back-up zone 11 without any substantial rotational movement of the material therein. The guiding members 38 are preferably shaped as longitudinal ribs having rectangular cross-sections and extend radially, inwardly from the housing wall 6. Preferably, guiding members 38 are uniformly distributed along the inner peripheral surface of housing wall 6.

Figure 5:
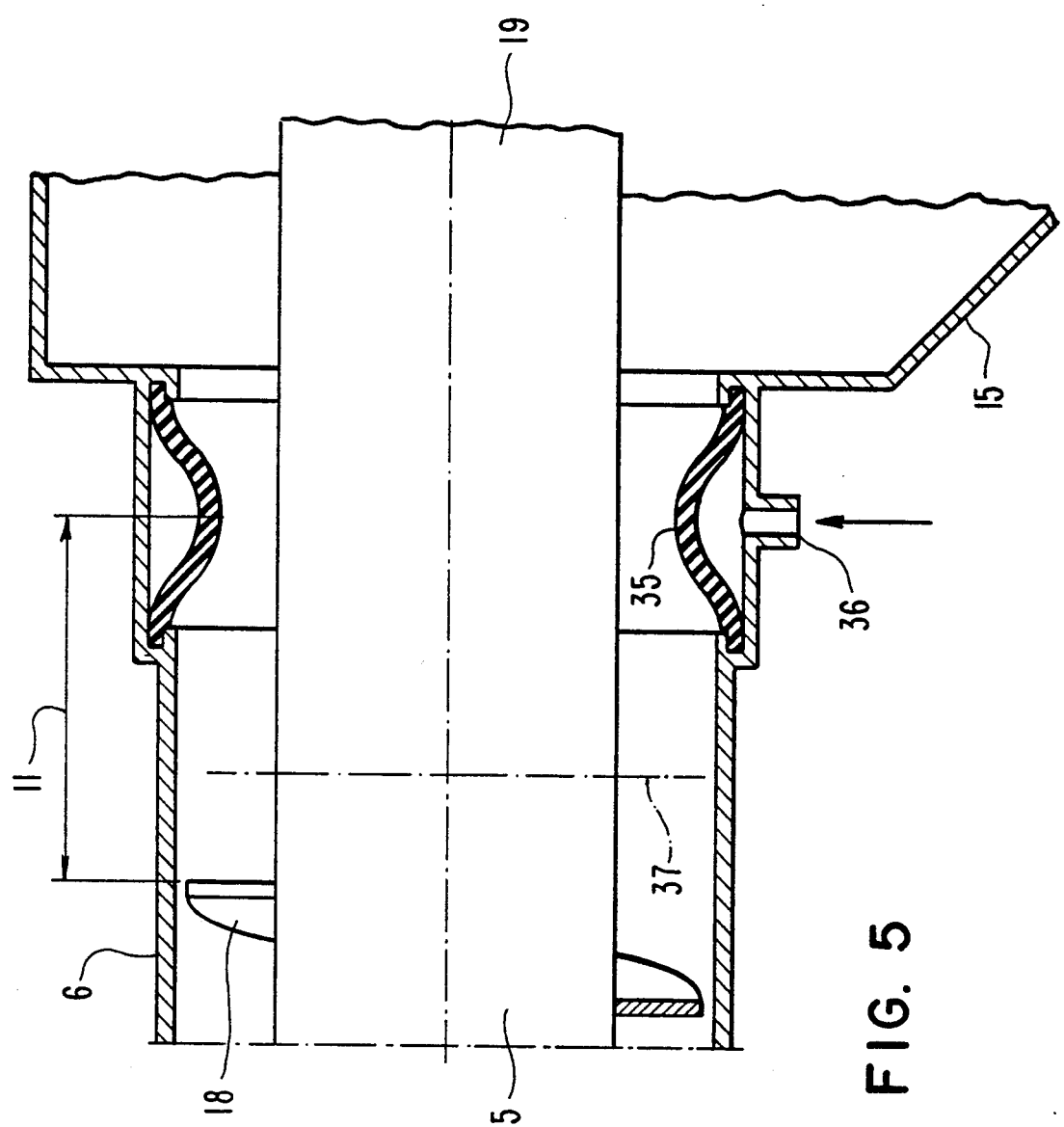

FIG. 5 illustrates yet another embodiment of enlarged sleeve portion 15. This embodiment includes annular bellows 35, charged with a pressure fluid, provided at the end of the measuring zone 11 in the housing 6. A hydraulic fluid is introduced via orifice 36 between annular bellows 35 and the housing wall. The material of the bellows is preferably elastic, for instance rubber or an elastomer (silicon rubber).

The annular gap between shaft 19 and bellows 35 is constricted by varying volumes depending on the amount of pressure fluid introduced so that the pressure in measuring zone 11 can be adjusted and/or maintained.

In FIGS. 3, 4 and 5, the measuring plane bears the reference number 37.

The gravity pit 16 extends from enlarged sleeve portion 15 to the top of the tower 1. Gravity pit 16 includes window 17 suitable for opening, as shown in FIG. 2. Window 17 can be employed for observing the dropping material, sample-taking, inspection or cleaning of the gravity pit 16. The conveyed material passes through annular gap 21 and drops back into the bleaching tower 1 via gravity pit 16. Gravity pit 16 also serves as a support for the sampling device 2.

The invention is not limited to the embodiments represented and described. For example, the rotatable disk or ring in sleeve portion 15 could be driven independently of the conveyor and at a variable speed.

In addition, the disk 20 according to FIG. 3 could be provided with ribs on its front side directed towards the measuring zone 11. The ribs could convey the material in the measuring zone radially outwards, i.e., to and through the gap 21, due to the rotation of the disk 20. This is advantageous if the disk is driven independently of the conveyor and affords a further possibility of adjusting and controlling the pressure in the measuring zone.

FIGS. 1 to 5 show that the conveyor can extend through the back-up zone but be formed there in such a manner that the conveyor develops a certain conveying energy there.

Various modifications, improvements and other embodiments will become apparent to those skilled in the art once given this disclosure. Such modifications, improvements and other embodiments are considered to be within the scope of this invention as defined by the following claims.

What is claimed is:

1. An apparatus for determining the properties of a compactible material, comprising:
   a housing having an inlet, an outlet and a measuring zone located between said inlet and outlet;
   conveying means, coupled to said housing and adapted to be positioned in a body of a compactible material for substantially continuously removing a sample portion of the compactible material from the body of compactible material and conveying the sample portion through said measuring zone of said housing;
   sensing means, coupled to said measuring zone of said housing, for determining properties of the compactible material; and
   back pressure means, located in said housing, for applying a pressure on the sample portion of the compactible material in said measuring zone of said housing, said back pressure means including a disk biased against the flow of the compactible material by at least one spring.

2. The apparatus according to claim 1, wherein said at least one spring comprises a plurality of springs adjustably coupled relative to said housing for varying the pressure applied on the sample portion of compactible material.

3. The apparatus according to claim 2, further comprising means to adjust the tension of said at least one spring.

4. The apparatus according to claim 3, wherein the adjusting means is at least one bolt operatively coupled to said at least one spring.

5. An apparatus for determining the properties of a compactible material, comprising:
   a housing having an inlet, an outlet and a measuring zone located between said inlet and outlet;
   conveying means, coupled to said housing and adapted to be positioned in a body of a compactible material, for substantially continuously removing a sample portion of the compactible material from the body of compactible material and for conveying the sample portion through said measuring zone of said housing;
   sensing means, coupled to said measuring zone of said housing, for determining properties of the compactible material; and
   back pressure means, located in said housing, for applying a pressure on the sample portion of the compactible material in said measuring zone of said housing, said back pressure means including a disk biased against the flow of the compactible material by at least one spring, and said disk being rotatably driven by said conveying means.

6. The apparatus according to claim 5, wherein said conveying means is an auger type conveyor with a longitudinal axis.

7. The apparatus according to claim 4, wherein
   said at least one spring is concentrically mounted on said auger type conveyor about a central longitudinal axis thereof.

8. An apparatus for determining the properties of a compactible material, comprising:
   a housing having an inlet, an outlet and a measuring zone located between said inlet and outlet;
   conveying means, coupled to said housing and adapted to be positioned in a body of a compactible material, for substantially continuously removing a sample portion of the compactible material from the body of compactible material and for conveying the sample portion through said measuring zone of said housing;
   sensing means, coupled to said measuring zone of said housing, for determining properties of the compactible material; and
   back pressure means, located in said housing, for applying a pressure on the sample portion of the compactible material in said measuring zone of said housing, said back pressure means including an inflatable member located adjacent said conveying means for constricting a cross-sectional, interior portion of said housing.

9. The apparatus according to claim 8, wherein said inflatable member comprises an inflatable annular bellows coupled to said housing.

10. An apparatus for determining the properties of a compactible material, comprising:
    a housing having an inlet, and outlet and a measuring zone located between said inlet and outlet;
    conveying means, coupled to said housing and adapted to be positioned in a body of a compactible material, for substantially continuously removing a sample portion of the compactible material from the body of compactible material and for conveying the sample portion through said measuring zone of said housing;
    sensing means, couple to said measuring zone of said housing, for determining properties of the compactible material; and
    back pressure means, located in said housing, for applying a pressure on the sample portion of the compactible material in said measuring zone of said housing;
    said conveying means including an auger type conveyor having
      a first section with screw turns extending between said inlet of said housing and said measuring zone, and
      a second section with screw turns extending through said measuring zone said screw turns of said second section of said auger type conveyor having a lower pitch than said screw turns of said first section of said auger type conveyor for subjecting the material to a comparatively low conveying energy in said measuring zone.

11. The apparatus according to claim 10, wherein said housing includes guiding means for controlling the movement of the material such that the material moves axially through said measuring zone without any substantial rotational movement of the material in said measuring zone.

12. An apparatus for determining the properties of a compactible material, comprising:

a housing having an inlet, an outlet and a measuring zone located between said inlet and outlet;

screw conveying means, coupled to said housing and adapted to be positioned in a body of a compactible material, for substantially continuously removing a sample portion of the compactible material from the body of compactible material and for conveying the sample portion through said measuring zone of said housing, said screw conveying means having screw turns;

sensing means, coupled to said measuring zone of said housing, for determining properties of the compactible material; and back pressure means, located in said housing, for applying a pressure on the sample portion of the compactible material in said measuring zone of said housing, said housing including guiding means, coupled to said housing and positioned axially adjacent along side said screw turns of said screw conveying means, for controlling the movement of the material such that the material moves axially through said measuring zone without any substantial rotational movement of the material in said measuring zone.

* * * * *